US012557970B2

(12) United States Patent
Desai et al.

(10) Patent No.: US 12,557,970 B2
(45) Date of Patent: Feb. 24, 2026

(54) STEERABLE AND FLEXIBLE ROBOTIC ENDOSCOPIC TOOLS FOR MINIMALLY INVASIVE PROCEDURES

(71) Applicant: Georgia Tech Research Corporation, Atlanta, GA (US)

(72) Inventors: Jaydev P. Desai, Atlanta, GA (US); Yash Chetan Chitalia, Atlanta, GA (US); Seokhwan Jeong, Atlanta, GA (US); Joshua J. Chern, Atlanta, GA (US)

(73) Assignee: GEORGIA TECH RESEARCH CORPORATION, Atlanta, GA (US)

( * ) Notice: Subject to any disclaimer, the term of this patent is extended or adjusted under 35 U.S.C. 154(b) by 0 days.

(21) Appl. No.: 19/196,285

(22) Filed: May 1, 2025

(65) Prior Publication Data

US 2025/0255466 A1 Aug. 14, 2025

Related U.S. Application Data

(62) Division of application No. 17/433,165, filed as application No. PCT/US2020/020942 on Mar. 4, 2020, now Pat. No. 12,318,067.

(Continued)

(51) Int. Cl.
*A61B 1/00* (2006.01)
*A61B 1/005* (2006.01)
(Continued)

(52) U.S. Cl.
CPC .......... *A61B 1/00087* (2013.01); *A61B 1/005* (2013.01); *A61B 1/0125* (2013.01); *A61B 1/018* (2013.01)

(58) Field of Classification Search
CPC ................ A61M 5/5013; A61M 5/502; A61M 2005/5033; A61B 1/005; A61B 1/0125; A61B 1/018
See application file for complete search history.

(56) References Cited

U.S. PATENT DOCUMENTS 4,632,110 A 12/1986 Sanagi
6,012,494 A 1/2000 Balazs
(Continued)

FOREIGN PATENT DOCUMENTS

DE 10 2009 037 030 A1 2/2011
JP 2014-000265 A 1/2014
(Continued)

OTHER PUBLICATIONS

Office Action dated Feb. 6, 2020 in corresponding Japanese Application No. 2021-553091 (with Machine Translation).
(Continued)

*Primary Examiner* — Dung T Ulsh
(74) *Attorney, Agent, or Firm* — TROUTMAN PEPPER LOCKE LLP; Ryan A. Schneider; Brandon M. Reed

(57) ABSTRACT

A probe part includes a base member defining a first bore. A first elongated elastic member includes a near end secured to the base member and extends therefrom to a far end and defines a channel in communication with the first bore and that runs lengthwise with the first elongated elastic member. A first tendon has a first end and an opposite second end that is secured to the first elongated elastic member adjacent to the far end. The first tendon runs through the channel adjacent the first side and exits through the first bore exiting outwardly therefrom. Applying tension to the first tendon causes the first elongated elastic member to bend in the direction of the first side.

10 Claims, 8 Drawing Sheets

Related U.S. Application Data

(60) Provisional application No. 62/813,444, filed on Mar. 4, 2019.

(51) Int. Cl.
  *A61B 1/012* (2006.01)
  *A61B 1/018* (2006.01)

(56) References Cited

U.S. PATENT DOCUMENTS

| | | | |
|---|---|---|---|
| 6,749,560 | B1 | 6/2004 | Konstorum et al. |
| 10,321,804 | B2 | 6/2019 | Jacobsen et al. |
| 10,617,438 | B2 | 4/2020 | O'Keefe et al. |
| 2001/0037084 | A1 | 11/2001 | Nardeo |
| 2005/0096694 | A1 | 5/2005 | Lee |
| 2005/0159645 | A1* | 7/2005 | Bertolero ........... A61B 1/00142 600/116 |
| 2007/0021737 | A1 | 1/2007 | Lee |
| 2007/0225562 | A1 | 9/2007 | Spivey et al. |
| 2009/0062606 | A1 | 3/2009 | Ueda et al. |
| 2012/0053415 | A1 | 3/2012 | Bunch et al. |
| 2013/0197306 | A1 | 8/2013 | Armand et al. |
| 2014/0379000 | A1 | 12/2014 | Romo et al. |
| 2017/0065153 | A1 | 3/2017 | Fujitani |
| 2018/0228346 | A1 | 8/2018 | Sekowski et al. |
| 2020/0221927 | A1 | 7/2020 | Matthison-Hansen |
| 2020/0268238 | A1 | 8/2020 | Jensen et al. |
| 2020/0281666 | A1 | 9/2020 | Gunn et al. |

FOREIGN PATENT DOCUMENTS

| | | |
|---|---|---|
| JP | 2014-090800 A | 5/2014 |
| JP | 2018-534052 A | 11/2018 |
| WO | 2017/213491 A1 | 12/2017 |

OTHER PUBLICATIONS

Supplementary European Search Report mailed Sep. 30, 2022 in corresponding European Application No. EP 20 76 6820.
International Search Report and Written Opinion mailed Jul. 24, 2020 in corresponding International Patent Application No. PCT/US2020/020942.

* cited by examiner

STEERABLE AND FLEXIBLE ROBOTIC ENDOSCOPIC TOOLS FOR MINIMALLY INVASIVE PROCEDURES

CROSS-REFERENCE TO RELATED APPLICATIONS

This Application is a divisional of U.S. patent application Ser. No. 17/433,165 filed 23 Aug. 2021, which U.S. patent application Ser. No. 17/433,165 is a § 371 National Stage of International Patent Application No. PCT/US2020/020942, with an international filing date of 4 Mar. 2020, which International Patent Application No. PCT/US2020/020942 claims the benefit under 35 USC § 119(c) of U.S. Provisional Patent Application No. 62/813,444 filed 4 Mar. 2019, the entire contents and substance of being incorporated herein by reference in its entirety as if fully set forth below.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

SEQUENCE LISTING

Not Applicable

STATEMENT REGARDING PRIOR DISCLOSURES BY THE INVENTOR OR A JOINT INVENTOR

Not Applicable

BACKGROUND OF THE DISCLOSURE

1. Field of the Disclosure

The present invention relates to endoscopic tools and, more specifically, to a steerable probe part.

2. Background

Hydrocephalus is a common pediatric disease occurring at a rate of about 0.7 cases per thousand in most developed countries. This number is even higher in developing countries. This condition occurs due to a buildup of cerebrospinal fluid (CSF) in the brain leading to the enlargement of the ventricles and intracranial pressure increase. CSF is believed to be produced in the lateral ventricles, passing successively through the third ventricle, cerebral aqueduct, fourth ventricle prior to its exit into the cisternal spaces around the cranio-cervical junction.

One of the most common causes of hydrocephalus is due to blockage of CSF circulation at the level of the cerebral aqueduct, which connects the third and fourth ventricles. Delay in the treatment of hydrocephalus can result in the loss of motor function, epilepsy, chronic headaches, sensory damage and death. Most commonly, clinicians would treat hydrocephalus by diverting the CSF through implantation of a silicone tubing between the brain and the abdomen (CSF shunts). However, six decades worth of experiences with CSF shunts have shown that they are imperfect devices, with the blockage of shunts being the number one cause of morbidity and mortality.

An alternative to CSF shunt placement were brain endoscopic procedures with the purpose of removing the blockage or bypassing the blockage within the brain, thus avoiding implantation of a CSF shunt altogether. One of the most common brain endoscopic procedures is the endoscopic third ventriculostomy (ETV). During ETV, the surgeon first makes an entry into the ventricle using an endoscope, composed of a high definition camera and a light source. Under direct visualization, the surgeon then makes a perforation on the floor bottom wall of the third ventricle using a rigid instrument passed through the working channel of the endoscope. This perforation allows the CSF to bypass the blockage at the cerebral aqueduct and to egress into the prepontine cisterns located under the third ventricle. While this procedure has seen a success rate of over 80% in infants, reaching a suitable location in the third ventricle for penetration in an ETV procedure can be difficult.

Because of the rigid nature of the endoscope, a linear pathway from the scalp, through the brain parenchyma, down to the level of the third ventricular floor is required. This linear pathway must avoid traversing important blood vessels, functional areas and cranial nerves to avoid hemorrhaging. Further complicating the issue is the fact that the brain anatomy is often distorted due to the disease process. Because of all these restrictions, finding an optimal linear pathway may not always be possible.

Therefore, there is a need for steerable endoscopic probe assembly that can avoid obstacles.

BRIEF SUMMARY OF THE DISCLOSURE

The disadvantages of the prior art are overcome by the present invention which, in an exemplary embodiment, is a probe assembly comprising a first elongated elastic member having a first side and an opposite second side, including a near end secured to the base member and extending therefrom to a far end, and defining a first channel in communication with the first bore running lengthwise along the first elongated elastic member, one or more additional elongated elastic members coupled in series to the first elongated elastic member, each additional elongated elastic member having a first side and an opposite second side, including a near end and extending to an opposite far end, and defining an additional channel running lengthwise along the additional elongated elastic member, and an intermediate rigid member affixed to the far end of each of the first and additional elongated elastic members.

In any of the embodiments disclosed herein, the probe assembly can further comprise a base member defining a first bore and a spaced apart second bore passing therethrough, a first tendon having a first end located outside the base member, the first tendon having a portion which is disposed through the first bore which is adjacent to the first side of the first elongated elastic member, and the first tendon having a portion extending to an opposite second end located within the first channel of the first elongated elastic member, the second end of the first tendon being secured to the first elongated elastic member adjacent to the far end, the first tendon exiting through the first bore so that the first end extends outwardly therefrom, such that applying tension to the first tendon causes the first elongated elastic member to bend in the direction of the first side of the first elongated elastic member, and a second tendon having a first end located outside the base member, the second tendon having a portion which is disposed through the second bore which is adjacent to the second side of the first elongated elastic member, and the second tendon having a portion extending to an opposite second end located within the first channel of the first elongated elastic member, the second end of the second tendon being secured to the first elongated elastic member adjacent to the far end, the second tendon exiting through the second bore so that the first end extends outwardly therefrom, such that applying tension to the second tendon causes the first elongated elastic member to bend in the direction of the second side of the first elongated elastic member.

In any of the embodiments disclosed herein, the probe assembly can further comprise a third tendon, wherein a first of the one or more additional elongated elastic members is a second elongated elastic member, and the third tendon having a first end located outside the base member, the third tendon having a portion which is disposed through a third bore in the base member, which is adjacent to the first side of the second elongated elastic member, and the third tendon having a portion extending to an opposite second end located within the additional channel of the second elongated member, the second end of the third tendon secured to the second elongated elastic member adjacent to the far end, the third tendon exiting through the third bore so that the first end extends outwardly therefrom, such that applying tension to the third tendon causes the second elongated elastic member to bend in the direction of the first side of the second elongated elastic member.

In any of the embodiments disclosed herein, the probe assembly can further comprise a fourth tendon having a first end located outside the base member, the fourth tendon having a portion which is disposed through a fourth bore in the base member, which is adjacent to the second side of the second elongated elastic member, and the fourth tendon having a portion extending to an opposite second end located within the additional channel of the second elongated member, the second end of the fourth tendon secured to the second elongated elastic member adjacent to the far end, the fourth tendon exiting through the fourth bore so that the first end extends outwardly therefrom, such that applying tension to the fourth tendon causes the second elongated elastic member to bend in the direction of the second side of the second elongated elastic member.

In any of the embodiments disclosed herein, the probe part can have a diameter that is less than a working channel of a rigid endoscope.

In any of the embodiments disclosed herein, the first elongated elastic member can further comprise a first tube including a first tube first plurality of crenulations machined into the first side of the first elongated elastic member.

In any of the embodiments disclosed herein, the second elongated elastic member can further comprise a second tube including a second tube first plurality of crenulations machined into the first side of the second elongated elastic member.

In any of the embodiments disclosed herein, the first tube can further include a first tube second plurality of crenulations machined into the second side of the first elongated elastic member.

In any of the embodiments disclosed herein, the second tube can further include a second tube second plurality of crenulations machined into the second side of the second elongated elastic member.

In any of the embodiments disclosed herein, the probe assembly can further comprise a tool affixed to the far end of the second elongated elastic member.

In an exemplary embodiment, the present invention is a probe system comprising the probe assembly of any of the embodiments disclosed herein, and a device configured to operate the probe assembly, wherein the device is further configured to be used with an endoscope that defines a lengthwise passage passing therethrough, the device comprises a housing having an interior that is configured to be accessed by retracting a retractable portion, the housing further having an end that is configured for joining with the endoscope, at least one input passage defined by the housing and configured to be aligned with the lengthwise passage of the endoscope, the at least one input passage configured to receive a portion of the probe assembly therein so that the probe assembly is received into the lengthwise passage of the endoscope, and an actuator assembly affixed to the housing and configured to manipulate the probe assembly by selectively applying stress to one or more of the first or second tendons.

In any of the embodiments disclosed herein, the device can further comprise a quick connect assembly couplable to the actuator assembly and affixed to the probe assembly, wherein one or more of the first or second tendons is coupled to a probe-side tendon connector, and the actuator assembly includes an actuator-side tendon connector that is complimentary to the probe-side tendon connector so that when the quick connect assembly is snapped in place with the actuator assembly, the actuator-side tendon connector engages the probe-side tendon connector so that actuator-induced movements applied to the actuator-side tendon connector results in corresponding movements in the probe-side tendon connector, thereby resulting in manipulation of the one or more of the first or second tendons.

In any of the embodiments disclosed herein, the probe system can further comprise at least one joystick configured to provide intuitive control input to the probe assembly.

In an exemplary embodiment, the present invention is a device for operating a probe assembly having directional control as a result of applying stress to at least one tendon, the device configured to be used with an endoscope that defines a lengthwise passage passing therethrough, the device comprising a housing having an interior that is configured to be accessed by retracting a retractable portion, the housing having an end that is configured for joining with an endoscope, at least one input passage defined by the housing and configured to be aligned with the lengthwise of the endoscope, the at least one input passage configured to receive a portion of the probe assembly therein so that the probe assembly is received into the lengthwise passage of the endoscope, and an actuator assembly affixed to the housing and configured to manipulate the probe assembly by selectively applying stress to the at least one tendon.

In any of the embodiments disclosed herein, the device can further comprise a quick connect assembly couplable to the actuator assembly and affixed to the probe assembly, wherein the at least one tendon is coupled to a probe-side tendon connector, and the actuator assembly includes an actuator-side tendon connector that is complimentary to the probe-side tendon connector so that when the quick connect assembly is snapped in place with the actuator assembly, the actuator-side tendon connector engages the probe-side tendon connector so that actuator-induced movements applied to the actuator-side tendon connector results in corresponding movements in the probe-side tendon connector, thereby resulting in manipulation of the at least one tendon.

In any of the embodiments disclosed herein, the device can further comprise at least one joystick configured to provide intuitive control input to the probe assembly.

In another exemplary embodiment, the present invention is a probe part that includes a base member defining a first bore passing therethrough. A first elongated elastic member has a first side and an opposite second side, the first elongated elastic member includes a near end secured to the base member and extends therefrom to a far end. The first elongated elastic member defines a first channel that is in communication with the first bore and that runs lengthwise along the first elongated elastic member. A first tendon, a portion of which is disposed in the first channel adjacent to the first side of the first elongated elastic member, has a first end and an opposite second end. The second end is secured to the first elongated elastic member adjacent to the far end. The first tendon exits through the first bore so that the first end extends outwardly therefrom. Applying tension to the first tendon causes the first elongated elastic member to bend in the direction of the first side of the first elongated elastic member.

In another exemplary embodiment, the present invention is a probe assembly that includes a base member defining a first bore, a second bore, a third bore and a fourth bore passing therethrough. A first elongated elastic member has a first side and an opposite second side. The first elongated elastic member including a near end secured to the base member and extending therefrom to a far end. The first elongated elastic member defines a first passage aligned with the first bore and running lengthwise adjacent to the first side of the first elongated elastic member. The first elongated elastic member also defining a second passage aligned with the second bore and running lengthwise adjacent to the second side of the first elongated elastic member. An intermediate rigid member is affixed to the far end of the first elongated elastic member. A second elongated elastic member is affixed to the intermediate rigid member opposite from the first elongated elastic member. The second elongated elastic member has a first side and an opposite second side. The second elongated elastic member defines a third passage running lengthwise adjacent to the first side of the second elongated elastic member. The second elongated elastic member also defines a fourth passage running lengthwise adjacent to the second side of the first elongated elastic member. A first tendon has a first end and an opposite second end. The second end is secured to the first elongated elastic member adjacent to the far end. The first tendon runs through the first passage and exits through the first bore so that the first end extends outwardly therefrom.

Applying tension to the first tendon causes the first elongated elastic member to bend in the direction of the first side of the first elongated elastic member. A second tendon has a first end and an opposite second end. The second end is secured to the first elongated elastic member adjacent to the far end. The second tendon runs through the second passage and exits through the second bore so that the first end extends outwardly therefrom. Applying tension to the second tendon causes the first elongated elastic member to bend in the direction of the second side. A third tendon has a first end and an opposite second end. The second end is secured to the second elongated elastic member adjacent to the far end. The third tendon runs through the third passage defined by the second elongated elastic member, through a third passage defined by the first elongated elastic member and exits through a third bore in the base member so that the first end extends outwardly therefrom. Applying tension to the third tendon causes the second elongated elastic member to bend in the direction of the first side of the second elongated elastic member. A fourth tendon has a first end and an opposite second end. The second end is secured to the second elongated elastic member adjacent to the far end. The fourth tendon runs through the fourth passage and exits through a fourth bore in the base member so that the first end extends outwardly therefrom. Applying tension to the fourth tendon causes the second elongated elastic member to bend in the direction of the second side of the second elongated elastic member.

In yet another exemplary embodiment, the present invention is a tool for operating a probe assembly that includes at least one elastic member having directional control as a result of applying stress to at least one tendon. The tool is configured to be used with an endoscope that defines a lengthwise passage passing therethrough. A housing has an interior that is configured to be accessed by retracting a retractable portion. The housing has an end that is configured for joining with an endoscope. At least one input passage is defined by the housing and is configured to be aligned with the lengthwise of the endoscope. The at least one input passage is configured to receive a portion of the at least one tendon therein so that the at least one elastic member is received into the lengthwise passage defined by the endoscope. An actuator assembly is affixed to the housing and is configured to manipulate the at least one tendon by selectively applying stress thereto.

In another exemplary embodiment, the present invention is a probe part configured to pass through a proximal end of an endoscope, though a working channel of the endoscope, and beyond a distal end of the endoscope, the probe part having a proximal end and a distal end, the probe part configured to locate the distal end of the probe part to a destination location beyond the distal end of the endoscope, the probe part comprising a base member defining a first bore and a spaced apart second bore passing therethrough, a first elongated elastic member having a first side and an opposite second side, including a near end secured to the base member and extending therefrom to a far end, and defining a first channel in communication with the first bore running lengthwise along the first elongated elastic member, a second elongated elastic member having a first side and an opposite second side, including a near end and extending to an opposite far end, defining a second channel in communication with the first channel running lengthwise along the second elongated elastic member, an inter-joint coupling intermediate member that couples the second elongated elastic member to the first elongated elastic member, and provides an intermediate portion channel between the first and second channels.

In an exemplary embodiment, the probe part can further comprise a first tendon having a first end located outside the base member, the first tendon having a portion which is disposed through the first bore which is adjacent to the first side of the first elongated elastic member, and the first tendon having a portion extending to an opposite second end located within the first channel of the first elongated elastic member, the second end of the first tendon being secured to the first elongated elastic member adjacent to the far end, the first tendon exiting through the first bore so that the first end extends outwardly therefrom, such that applying tension to the first tendon causes the first elongated elastic member to bend in the direction of the first side of the first elongated elastic member.

In an exemplary embodiment, the probe part can further comprise a second tendon having a first end located outside the base member, the second tendon having a portion which is disposed through the second bore which is adjacent to the second side of the first elongated elastic member, and the second tendon having a portion extending to an opposite second end located within the first channel of the first elongated elastic member, the second end of the second tendon being secured to the first elongated elastic member adjacent to the far end, the second tendon exiting through the second bore so that the first end extends outwardly therefrom, such that applying tension to the second tendon causes the first elongated elastic member to bend in the direction of the second side of the first elongated elastic member.

In an exemplary embodiment, the probe part can have a diameter that is less than a working channel of a rigid endoscope.

In an exemplary embodiment, the first elongated elastic member can comprise a tube including a first plurality of crenulations machined into the first side of the first elongated elastic member.

In an exemplary embodiment, the tube can further include a second plurality of crenulations machined into the second side of the first elongated elastic member.

In an exemplary embodiment, the first plurality of crenulations can be symmetric with the second plurality of crenulations.

In an exemplary embodiment, the first plurality of crenulations can be asymmetric with the second plurality of crenulations.

In an exemplary embodiment, a tool affixed to the distal end of the probe part can be located to the destination, beyond the distal end of the endoscope.

In an exemplary embodiment, the probe part can further comprise a third tendon having a first end located outside the base member, the third tendon having a portion which is disposed through a third bore in the base member, which is adjacent to the first side of the second elongated elastic member, and the third tendon having a portion extending to an opposite second end located within the second channel of the second elongated member, the second end of the third tendon secured to the second elongated elastic member adjacent to the far end, the third tendon exiting through the third bore so that the first end extends outwardly therefrom, such that applying tension to the third tendon causes the second elongated elastic member to bend in the direction of the first side of the second elongated elastic member.

In an exemplary embodiment, the second elongated elastic member can comprise a tube including a first plurality of crenulations machined into the first side of the second elongated elastic member.

In an exemplary embodiment, the probe part can further comprise a fourth tendon having a first end located outside the base member, the fourth tendon having a portion which is disposed through a fourth bore in the base member, which is adjacent to the second side of the second elongated elastic member, and the fourth tendon having a portion extending to an opposite second end located within the second channel of the second elongated member, the second end of the fourth tendon secured to the second elongated elastic member adjacent to the far end, the fourth tendon exiting through the fourth bore so that the first end extends outwardly therefrom, such that applying tension to the fourth tendon causes the second elongated elastic member to bend in the direction of the second side of the second elongated elastic member.

In an exemplary embodiment, the tube can further include a second plurality of crenulations machined into the second side of the second elongated elastic member.

In an exemplary embodiment, the first plurality of crenulations can be symmetric with the second plurality of crenulations.

In an exemplary embodiment, the first plurality of crenulations can be asymmetric with the second plurality of crenulations.

In an exemplary embodiment, a tool affixed to the distal end of the probe part can be located to the destination, beyond the distal end of the endoscope.

In an exemplary embodiment, the at least one of the elongated elastic members can comprise a plurality of bidirectional asymmetric crenulations machined into the sides.

In an exemplary embodiment, the presence of the bidirectional asymmetric crenulations can keep sufficient compliance in the bending plane high, while also keeping external forces low.

In an exemplary embodiment, the bidirectional asymmetric crenulations can create a compliant bending length of the respective one or both of the elongated elastic members, capable of withstanding high axial forces as well as forces in the plane transverse to the bending plane, which resists transverse forces and allows for the tendon routing strategy to minimize inter joint coupling.

In an exemplary embodiment, the elongated elastic members can comprise nickel titanium alloy tubes.

In an exemplary embodiment, the bidirectional asymmetric crenulations can be micromachined with a femtosecond laser.

In another exemplary embodiment, the present invention is a probe part configured to pass through a proximal end of an endoscope, though a working channel of the endoscope, and beyond a distal end of the endoscope, the probe part having a proximal end and a distal end, the probe part configured to locate the distal end of the probe part to a destination location beyond the distal end of the endoscope, the probe part comprising a base member defining a first bore and a spaced apart second bore passing therethrough, a first elongated elastic member having a first side and an opposite second side, the first elongated elastic member including a near end secured to the base member and extending therefrom to a far end, the first elongated elastic member defining a first channel in communication with the first bore, running lengthwise along the first elongated elastic member, a second elongated elastic member having a first side and an opposite second side, the second elongated elastic member including a near end and extending to opposite far end, the second elongated elastic member defining a second channel in communication with the first channel, running lengthwise along the second elongated elastic member, an inter-joint coupling intermediate member that couples the second elongated elastic member to the first elongated elastic member and provides an intermediate portion channel between the first and second channels, a first tendon disposed in the first channel adjacent to the first side of the first elongated elastic member, passing through the inter-joint coupling intermediate member and passing through the second channel adjacent to the second side of the second elongated elastic member, and a second tendon disposed in the first channel adjacent to the second side of the first elongated elastic member, passing through the inter-joint coupling intermediate member and passing through the second channel adjacent to the first side of the second elongated elastic member, wherein the inter-joint coupling intermediate member phase-shifts the first tendon and the second tendon so that applying tension to at least one of the first tendon or the second tendon causes the first elongated elastic member to bend along a first plane and the second elongated elastic member to bend along a second plane that is transverse to the first plane, at least one of the elongated elastic members comprise a plurality of bidirectional asymmetric crenulations machined into the sides, the presence of the bidirectional asymmetric crenulations keeps sufficient compliance in the bending plane high, while also keeping external forces low, the bidirectional asymmetric crenulations create a compliant bending length of one or both of the elongated elastic members, capable of withstanding high axial forces as well as forces in the plane transverse to the bending plane, which resists transverse forces and allows for the tendon routing strategy to minimize inter joint coupling, the elongated elastic members comprise nickel titanium alloy tubes, and the bidirectional asymmetric crenulations are micromachined with a femtosecond laser.

In another exemplary embodiment, the present invention is a device for operating a probe assembly, the device configured to be used with the endoscope that defines a working channel as a lengthwise passage passing through the endoscope, the device comprising a housing having an interior that is configured to be accessed by retracting a retractable portion, the housing having an end that is configured for joining with an endoscope, at least one input passage defined by the housing and configured to receive a portion of the probe assembly therein so that the probe assembly is received into the lengthwise passage defined by the endoscope, and an actuator assembly affixed to the housing and configured to manipulate the probe assembly by selectively applying stress to the tendons of the probe part.

In an exemplary embodiment, the device can further comprise a quick connect assembly comprising a probe-side tendon connector, the quick connect assembly couplable to the actuator assembly and affixed to the probe assembly.

In an exemplary embodiment, the actuator assembly can comprise an actuator-side tendon connector.

In an exemplary embodiment, the tendons of the probe part can be coupled to the probe-side tendon connector.

In an exemplary embodiment, the actuator-side tendon connector can be complimentary to the probe-side tendon connector so that when the quick connect assembly is snapped in place with the actuator assembly, the actuator-side tendon connector engages the probe-side tendon connector so that actuator-induced movements applied to the actuator-side tendon connector results in corresponding movements in the probe-side tendon connector, thereby resulting in manipulation of the tendons of the probe part.

In an exemplary embodiment, the device can further comprise at least one joystick configured to provide intuitive control input to the probe assembly.

These and other aspects of the present disclosure are described in the Detailed Description below and the accompanying figures. Other aspects and features of embodiments of the present disclosure will become apparent to those of ordinary skill in the art upon reviewing the following description of specific, example embodiments of the present disclosure in concert with the figures. While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments of the disclosure discussed herein. In similar fashion, while example embodiments may be discussed below as device, system, or method embodiments, it is to be understood that such example embodiments can be implemented in various devices, systems, and methods of the present disclosure.

BRIEF DESCRIPTION OF THE DRAWINGS

The accompanying drawings, which are incorporated in and constitute a part of this specification, illustrate multiple embodiments of the presently disclosed subject matter and serve to explain the principles of the presently disclosed subject matter. The drawings are not intended to limit the scope of the presently disclosed subject matter in any manner.

DETAILED DESCRIPTION

Figures 1A, 1B, 2A, 2B, 2C, 3, 4A, 4B:
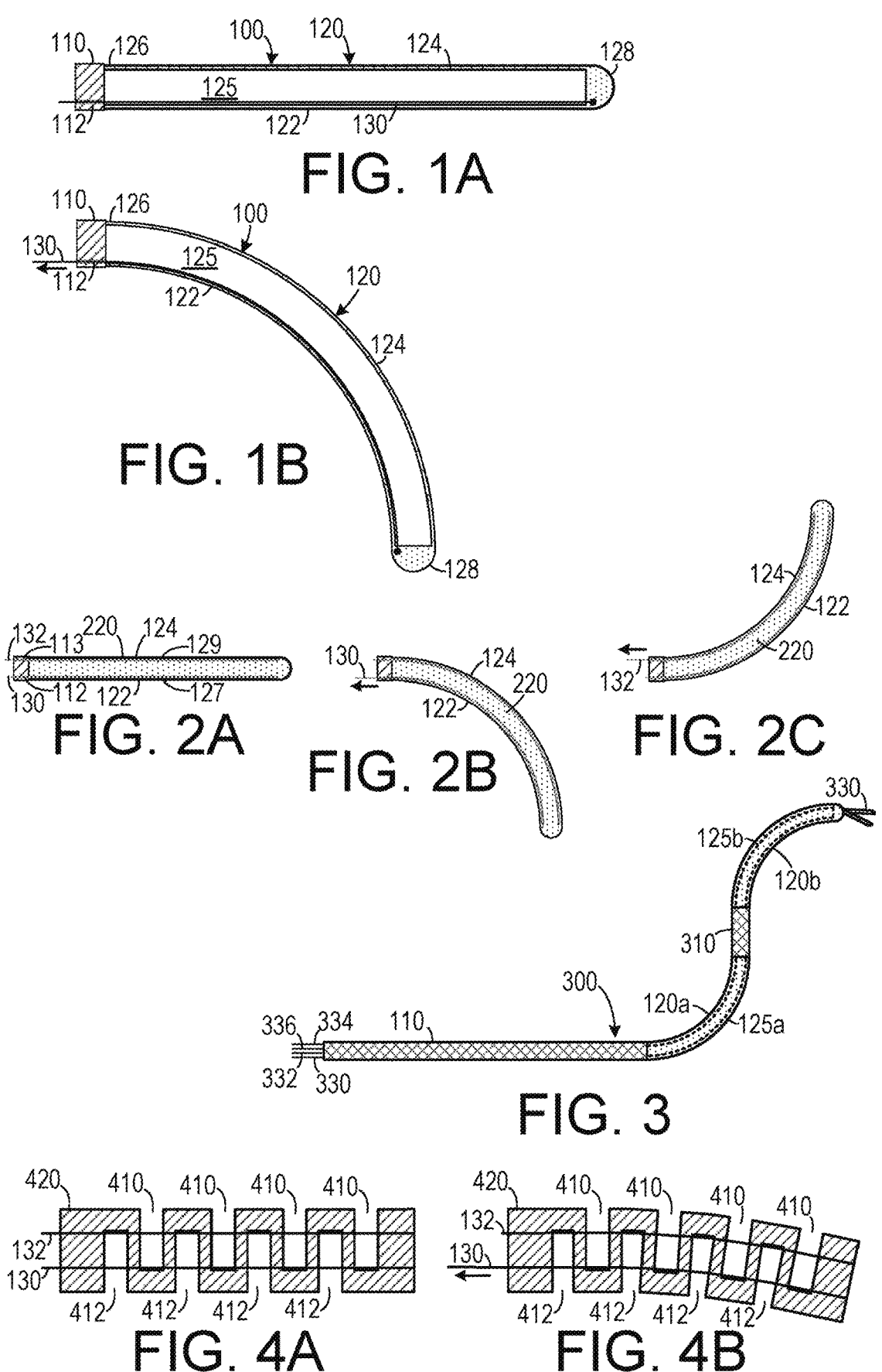
FIGS. 1A and 1B are schematic diagrams of one representative embodiment of a probe part according to an exemplary embodiment of the present invention.
FIGS. 2A-2C are schematic diagrams of a second embodiment of a probe part according to an exemplary embodiment of the present invention.
FIG. 3 is a schematic diagram of one embodiment of a probe according to an exemplary embodiment of the present invention.
FIGS. 4A-4B are schematic diagrams of a crenulated tube elastic member according to an exemplary embodiment of the present invention.

Although certain embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. Other embodiments of the disclosure are capable of being practiced or conducted in various ways. Also, in describing the embodiments, specific terminology will be resorted to for the sake of clarity. It is intended that each term contemplates its broadest meaning as understood by those skilled in the art and includes all technical equivalents which operate in a similar manner to accomplish a similar purpose.

It should also be noted that, as used in the specification and the appended claims, the singular forms "a," "an" and "the" include plural references unless the context clearly dictates otherwise. References to a composition containing "a" constituent is intended to include other constituents in addition to the one named.

Ranges may be expressed herein as from "about" or "approximately" or "substantially" one particular value and/ or to "about" or "approximately" or "substantially" another particular value. When such a range is expressed, other exemplary embodiments include from the one particular value and/or to the other particular value.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

It is also to be understood that the mention of one or more method steps does not preclude the presence of additional method steps or intervening method steps between those steps expressly identified. Moreover, although the term "step" may be used herein to connote different aspects of methods employed, the term should not be interpreted as implying any particular order among or between various steps herein disclosed unless and except when the order of individual steps is explicitly required.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter. Additionally, the components described herein may apply to any other component within the disclosure. Merely discussing a feature or component in relation to one embodiment does not preclude the feature or component from being used or associated with another embodiment.

A preferred embodiment of the present invention is now described in detail. Referring to the drawings, like numbers indicate like parts throughout the views. Unless otherwise specifically indicated in the disclosure that follows, the drawings are not necessarily drawn to scale. The present disclosure should in no way be limited to the exemplary implementations and techniques illustrated in the drawings and described below. As used in the description herein and throughout the claims, the following terms take the meanings explicitly associated herein, unless the context clearly dictates otherwise: the meaning of "a," "an," and "the" includes plural reference, the meaning of "in" includes "in" and "on."

A robotically-operable steerable probe assembly of the present invention is designed to fit in the small diameters of the working channels in commonly used endoscopes (such as the MINOP endoscope available from Acsculap Inc., which has a 2.2 mm working channel or the HandyPro endoscope available from Karl Storz SE & Co. KG with a 1.3 mm working channel). It is also designed to be highly maneuverable in its workspace, so that it can have a higher chance of avoiding obstacles. Also, in the operating room, it is often desirable to have two surgeons participating in endoscopic surgeries, where one surgeon directs the endoscope, inserting and retracting the scope body, while the other surgeon operates the instrument itself, including the insertion, retraction and rotation of the tool in the working channel of the endoscope. As a result, a robotic solution should include an actuator that can be operated in a small hand-held package.

The robotic probe system of the present invention includes three major components: a compliant elongated elastic member proximal joint that is highly resistive to transverse forces; a tendon phase shifting unit, that allows the distal tendons to be rerouted such that inter-joint coupling is minimized; and a highly compliant elongated elastic member distal joint.

As shown in FIG. 1, one embodiment of a probe part 100 includes a base member 110 that has a first bore 112 passing therethrough. A first elongated elastic member 120 (also referred to herein as a "joint") extends from the base member 110 and has a first side 122, an opposite second side 124 a near end 126 and a far end 128. The first elongated elastic member 120 defines a channel 125 that extends along the first side 122 and that is in alignment with the bore 112. A first tendon 130 runs through the bore 112 and the channel 125 and is secured to the first elongated clastic member 120 near the far end 128. As shown in FIG. 1B, applying stress to the first tendon 130 in the direction shown results in the first elongated elastic member 120 being bent inwardly in the direction of the first side 122.

As shown in FIGS. 2A-2C, the first elongated elastic member 220 can also define a first passage 127 and a second passage 129 along the second side and the base member can define a second bore 113 through which a second tendon 132 runs. This embodiment allows the first elongated clastic member 120 to be bent in both the direction of the first side 122 and also in the direction of the second side 124 by pulling on the tendons. In one embodiment, the tendons may include nickel titanium alloy (such as Nitinol) wires (such as part number WSE000450000DG available from https:// shop.confluentmedical.com/). It is understood that the tendons may include other materials, including other types of lines, wires, cords, etc., depending upon the specific application, without departing from the scope of the present invention.

As shown in FIG. 3, a probe assembly 300 can include a first elongated elastic member 120a (controlled by tendons 330 and 332) and a second elongated elastic member 120b (controlled by tendons 334 and 336) that are separated by an intermediate rigid member 310 that is configured as a phase shifting unit. The first elongated clastic member 120a defines channel 125a and the second elongated elastic member defines channel 125b. This probe assembly 300 is able to achieve such configurations as the "S" curve shown. Additionally, a tool 330 may be affixed to the end of the probe assembly 300 (which can also include a passage for a line used to control the tool 330) for use in the application of the probe assembly 300. In certain embodiments, a plurality of elongated elastic members may be coupled in series and separated from each other by a corresponding plurality of intermediate rigid members to achieve more complex movement patterns in the probe assembly. While the elongated elastic members are shown as being substantially tubular, they may taper or vary in diameter along their length depending upon the specific application. In yet another embodiment, the elongated members may have a non-tubular structure, such as a rectangular beam.

As shown in FIGS. 4A-4B, the elongated elastic members can include an elastic tube 420 into which is machined a first set of crenulations 410 on one side and a second set of crenulations 412 on the other side. In one embodiment, the elastic tube 420 includes nickel titanium alloy. (It is understood that the elastic tube 420 may include other materials that exhibit elastic properties depending upon specific applications without departing from the scope of the present invention.) When one of the tendons 130, as shown in FIG. 4B, is pulled outwardly, then the adjacent crenulations 412 are bend so as to be compressed, thereby bending the elongated elastic member in the direction of the side of the tendon 130 to which tension is applied. Once the tension is released, then the elongated elastic member will resume its original shape due to the superelastic property of nickel titanium alloy. However, this motion capability can be observed in other materials as well and is not necessarily limited to nickel titanium alloy. Furthermore, the elastic member may be joined to a non-elastic member through micro-welds for lowering the component costs.

Figures 5A, 5B, 5C:
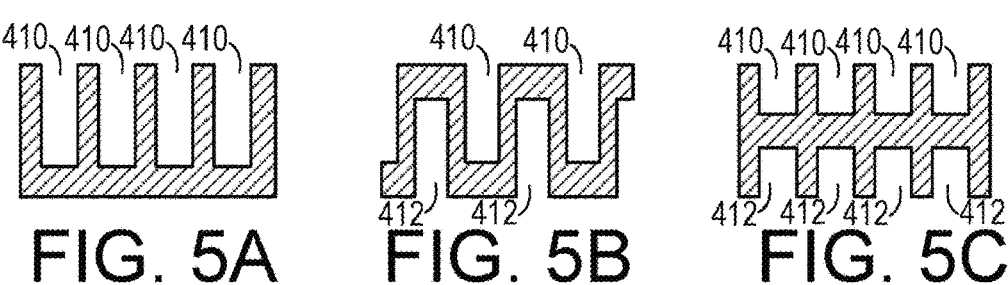
FIGS. 5A-5C are schematic diagrams of different crenulation patterns according to an exemplary embodiment of the present invention.
Figure 6:
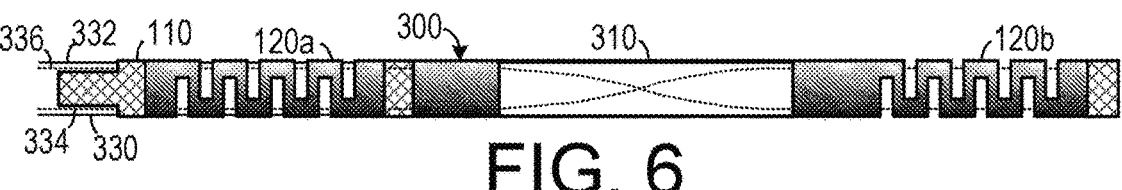
FIG. 6 is a schematic diagram of a probe employing crenulated elastic members according to an exemplary embodiment of the present invention.

FIG. 5A, shows a one-sided crenulation pattern, which allows bending in only one direction. FIG. 5B shows an asymmetric crenulation pattern and FIG. 5C shows a symmetric crenulation pattern, both of which allow bending in two directions. A probe assembly 200 employing crenulated elastic members 120 and 220 is shown in FIG. 6 (several other configurations are shown in FIGS. 14A-14D). Returning to FIG. 6, a portion of the inter-joint coupling intermediate member 310 is shown open to demonstrating phase-shifting routing of tendons 334 and 336.

Figures 7A, 7B, 7C:
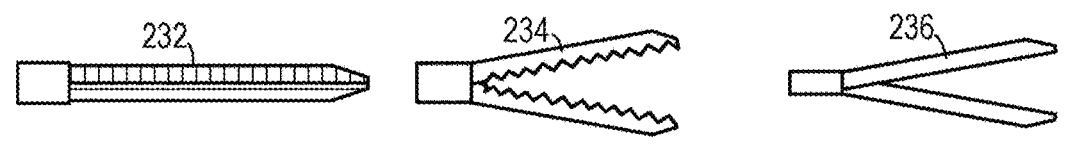
FIGS. 7A-7C are schematic diagrams of tools for use with probes according to an exemplary embodiment of the present invention.

Different tools are shown in FIGS. 7A-7C, which can include a bipolar electro-cautery tool 232, a gripping tool 234 and a scissor tool 236. It should be understood that other types of tools could also be employed, including, for example, an ablation tool, a basket tool, a loop tool, a knife tool, etc.

Figure 8:
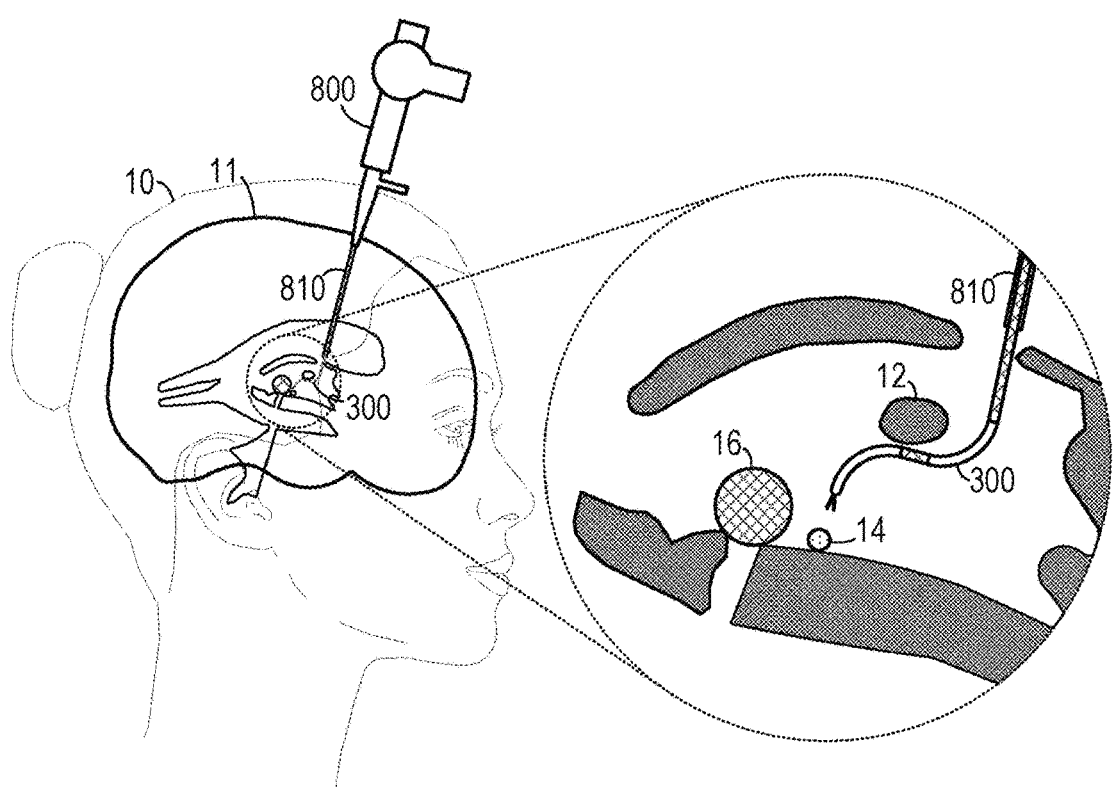
FIG. 8 is a schematic diagram that demonstrates use of a probe with an endoscope according to an exemplary embodiment of the present invention.

One embodiment of a probe assembly 300 being employed with a rigid endoscope 810 to perform an operation on the brain 11 of a patient 10 is shown in FIG. 8. This embodiment also shows an actuator assembly 800 used to control the probe assembly 300. As can be seen in the detail, the probe assembly 300 can be manipulated about obstructions 12 to reach a target area 14 for further manipulation to, for example, avoid a tumor 16.

As shown in the FIGS., the present invention can be a probe part 100 configured to pass through a proximal end of an endoscope, though a working channel of the endoscope, and beyond a distal end of the endoscope, the probe part 100 having a proximal end and a distal end, the probe part 100 configured to locate the distal end of the probe part to a destination location beyond the distal end of the endoscope, the probe part 100 comprising:

a base member 110 defining a first bore 112 and a spaced apart second bore 113 passing therethrough;

a first elongated elastic member 120a having a first side 122 and an opposite second side 124, the first elongated elastic member 120a including a near end 126 secured to the base member 110 and extending therefrom to a far end 128, the first elongated elastic member 120a defining a first channel 125a in communication with the first bore 112, running lengthwise along the first elongated elastic member 120a;

a second elongated elastic member 120b having a first side 122 and an opposite second side 124, the second elongated elastic member 120b including a near end 126 and extending to opposite far end 128, the second elongated elastic member 120b defining a second channel 125b in communication with the first channel 125a, running lengthwise along the second elongated elastic member 120b;

an inter-joint coupling intermediate member 310 that couples the second elongated elastic member 120b to the first elongated elastic member 120a;

a first tendon 330 having a first end located outside the base member 110, the first tendon 330 having a portion which is disposed through the first bore 112 which is adjacent to the first side 122 of the first elongated elastic member 120a, and the first tendon 330 having a portion extending to an opposite second end located within the first channel 125a of the first elongated elastic member 120a, the second end of the first tendon 330 being secured to the first elongated elastic member 120a adjacent to the far end 128, the first tendon 330 exiting through the first bore 112 so that the first end extends outwardly therefrom, such that applying tension to the first tendon 330 causes the first elongated elastic member 120a to bend in the direction of the first side 122 of the first elongated elastic member 120a; and a second tendon 332 having a first end located outside the base member 110, the second tendon 332 having a portion which is disposed through the second bore 113 which is adjacent to the second side 124 of the first elongated elastic member 120a, and the second tendon 332 having a portion extending to an opposite second end located within the first channel 125a of the first elongated elastic member 120a, the second end of the second tendon 332 being secured to the first elongated elastic member 120a adjacent to the far end 128, the second tendon 332 exiting through the second bore 113 so that the first end extends outwardly therefrom, such that applying tension to the second tendon 332 causes the first elongated elastic member 120a to bend in the direction of the second side 124 of the first elongated elastic member 120a.

An outer diameter of the probe part 100 can be less than the working channel of a rigid endoscope 810.

At least one of the elongated elastic members 120a, 120b can comprise along at least a portion of its length, a plurality of crenulations 410, 412 machined into at least one of the sides 122, 124.

At least one of the elongated elastic members 120a, 120b can comprise along at least a portion of its length, a first plurality of crenulations 410 machined into the first side 122 and a second plurality of crenulations 412 machined into the second side 124.

The first plurality of crenulations 410 can be symmetric with the second plurality of crenulations 412.

The first plurality of crenulations 410 can be asymmetric with the second plurality of crenulations 412.

A tool affixed to the distal end of the probe part 100 can be located to the destination, beyond the distal end of the endoscope.

The probe part 100 can further comprise a third tendon 334 having a first end located outside the base member 110, the third tendon 334 having a portion which is disposed through a third bore in the base member, which is adjacent to the first side 122 of the second elongated elastic member 120b, and the third tendon 334 having a portion extending to an opposite second end located within the second channel 125b of the second elongated member 120b, the second end of the third tendon secured to the second elongated clastic member 120b adjacent to the far end 128, the third tendon 334 exiting through the third bore so that the first end extends outwardly therefrom, such that applying tension to the third tendon 334 causes the second elongated elastic member 120b to bend in the direction of the first side 122 of the second elongated elastic member 120b.

At least one of the elongated clastic members 120a, 120b can comprise a plurality of bidirectional asymmetric crenulations 410, 412 machined into the sides 122, 124, wherein the presence of the bidirectional asymmetric crenulations 410, 412 keeps sufficient compliance in the bending plane high, while also keeping the effect of external forces low by manipulating the applied tendon tension, and wherein the bidirectional asymmetric crenulations 410, 412 create a compliant bending length of the respective one or both of the elongated elastic members 120a, 120b, capable of withstanding high axial forces as well as forces in the plane transverse to the bending plane, which resists transverse forces and allows for the tendon 330, 332, 334 routing strategy to minimize inter joint coupling.

The probe part can further comprise a fourth tendon 336 having a first end located outside the base member 110, the fourth tendon 336 having a portion which is disposed through a fourth bore in the base member, which is adjacent to the second side 124 of the second elongated elastic member 120b, and the fourth tendon 336 having a portion extending to an opposite second end located within the second channel 125b of the second elongated member 120b, the second end of the fourth tendon 336 secured to the second elongated clastic member 120b adjacent to the far end 128, the fourth tendon 336 exiting through the fourth bore so that the first end extends outwardly therefrom, such that applying tension to the fourth tendon 336 causes the second elongated elastic member 120b to bend in the direction of the second side 124 of the second elongated elastic member 120b.

At least one of the elongated elastic members 120a, 120b can comprise a plurality of bidirectional asymmetric crenulations 410, 412 machined into the sides 122, 124, wherein the presence of the bidirectional asymmetric crenulations 410, 412 keeps sufficient compliance in the bending plane high, while also keeping the effect of external forces low by manipulating the applied tendon tension, and wherein the bidirectional asymmetric crenulations 410, 412 create a compliant bending length of one or both of the elongated elastic members 120a, 120b, capable of withstanding high axial forces as well as forces in the plane transverse to the bending plane, which resists transverse forces and allows for the tendon 330, 332, 334, 336 routing strategy to minimize inter joint coupling.

The elongated elastic members 120a, 120b can comprise nickel titanium alloy tubes.

The bidirectional asymmetric crenulations 410, 412 can be micromachined with a femtosecond laser.

In another exemplary embodiment, the present invention is a probe part 100 configured to pass through a proximal end of an endoscope, though a working channel of the endoscope, and beyond a distal end of the endoscope, the probe part 100 having a proximal end and a distal end, the probe part 100 configured to locate the distal end of the probe part 100 to a destination location beyond the distal end of the endoscope, the probe part 100 comprising:

a base member 110 defining a first bore 112 and a spaced apart second bore 113 passing therethrough;

a first elongated elastic member 120a having a first side 122 and an opposite second side 124, the first elongated elastic member 120a including a near end 126 secured to the base member 110 and extending therefrom to a far end 128, the first elongated elastic member 120a defining a first channel 125a in communication with the first bore 112, running lengthwise along the first elongated elastic member 120a;

a second elongated elastic member 120b having a first side 122 and an opposite second side 124, the second elongated elastic member 120b including a near end 126 and extending to opposite far end 128, the second elongated elastic member 120b defining a second channel 125b in communication with the first channel 125a, running lengthwise along the second elongated elastic member 120b;

an inter-joint coupling intermediate member 310 that couples the second elongated elastic member 120b to the first elongated elastic member 120a;

a first tendon 130 disposed in the first channel 125a of the first elongated elastic member 120a, passing through the inter-joint coupling intermediate member 310 and passing through the second channel 125a of the second elongated elastic member 120b; and a second tendon 132 disposed in the first channel 125a of the first elongated elastic member 120a, passing through the inter-joint coupling intermediate member 310 and passing through the second channel 125a of the second elongated elastic member 120b;

wherein the inter-joint coupling intermediate member 310 phase-shifts the first tendon 130 and the second tendon 132 so that applying tension to at least one of the first tendon 130 or the second tendon 132 causes the first elongated elastic member 120a to bend along a first plane and the second elongated elastic member 120b to bend along a second plane that is transverse to the first plane;

wherein at least one of the elongated elastic members 120a, 120b comprise a plurality of bidirectional asymmetric crenulations 410, 412 machined into the sides 122, 124;

wherein the presence of the bidirectional asymmetric crenulations 410, 412 keeps sufficient compliance in the bending plane high, while also keeping the effect of external forces low by manipulating the applied tendon tension;

wherein the bidirectional asymmetric crenulations 410, 412 create a compliant bending length of one or both of the elongated elastic members 120a, 120b, capable of withstanding high axial forces as well as forces in the plane transverse to the bending plane, which resists transverse forces and allows for the tendon 130, 132 routing strategy to minimize inter joint coupling;

wherein the elongated elastic members 120a, 120b comprise nickel titanium alloy tubes; and wherein the bidirectional asymmetric crenulations 410, 412 are micromachined with a femtosecond laser.

Figure 9:
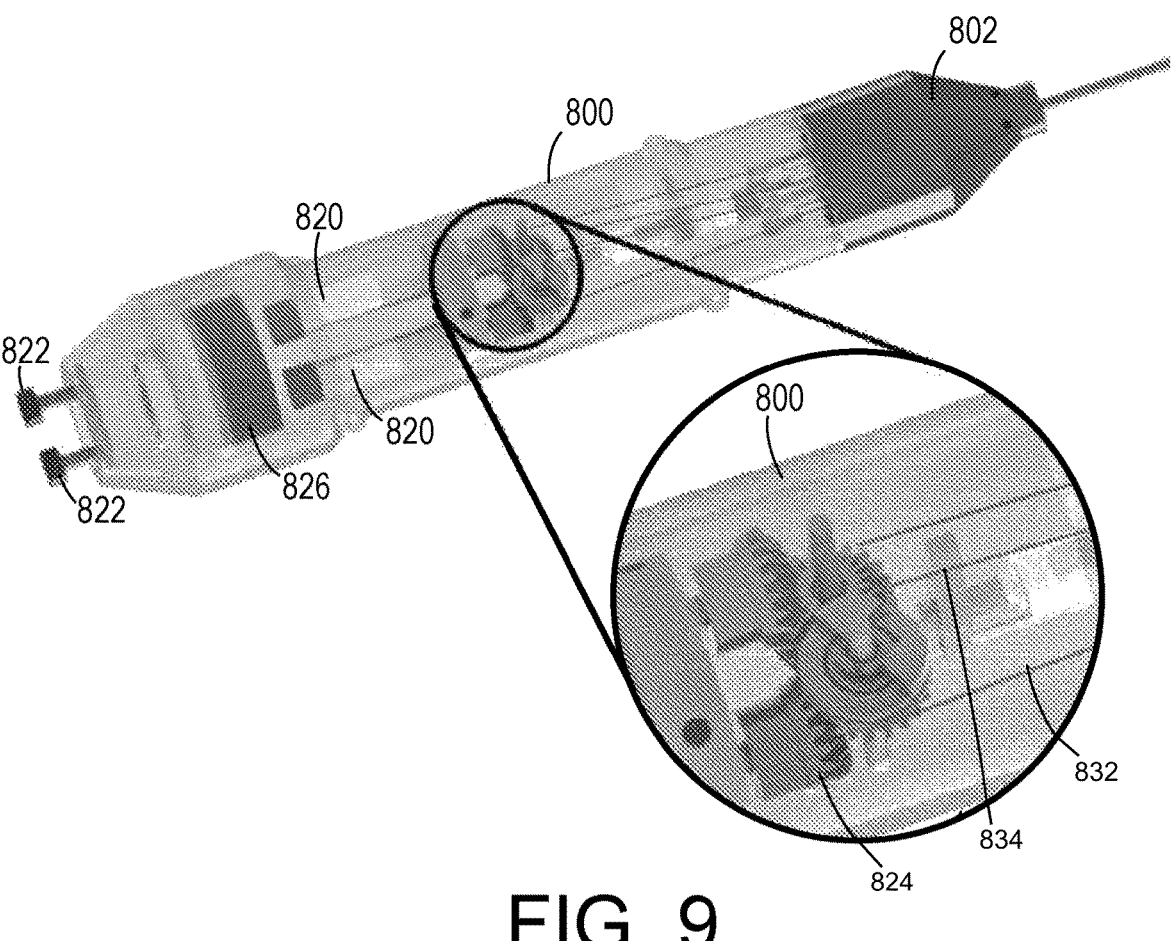
FIG. 9 is a schematic diagram of a probe controlling housing according to an exemplary embodiment of the present invention.
Figure 10:
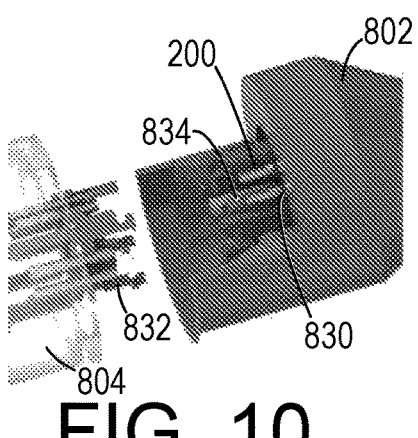
FIG. 10 is a detail of the housing shown in FIG. 9, showing probe connections according to an exemplary embodiment of the present invention.

The controller 800, as shown in FIG. 9, can employ two motors (or more) 820 that drive a gear assembly 824 that is used to apply tension to (and release tension from) the tendons. User operated joysticks 822 control movement of the motor 820. A circuit 826 is used to convey control commands from the joysticks 822 and a remote computer to the motors 820. This provides the user with intuitive control of the probe assembly. A quick connect assembly 802, as shown in FIG. 10, includes a retractable housing portion 804 that exposes input passages 830 into which the tendons (130, 132, 134 and 136) of the probe assembly 300 may be placed. (One embodiment includes two or more passages that would allow two or more probe assemblies to be placed therein, thereby allowing two or more tools to be passed through the endoscope.) Probe-side tendon connectors 834 engage actuator-side tendon connectors 832, which are manipulated by the pulley and gear assembly 824. The quick connect assembly 802 may be snapped in place with an insertion and twisting motion in one embodiment.

Figure 11:
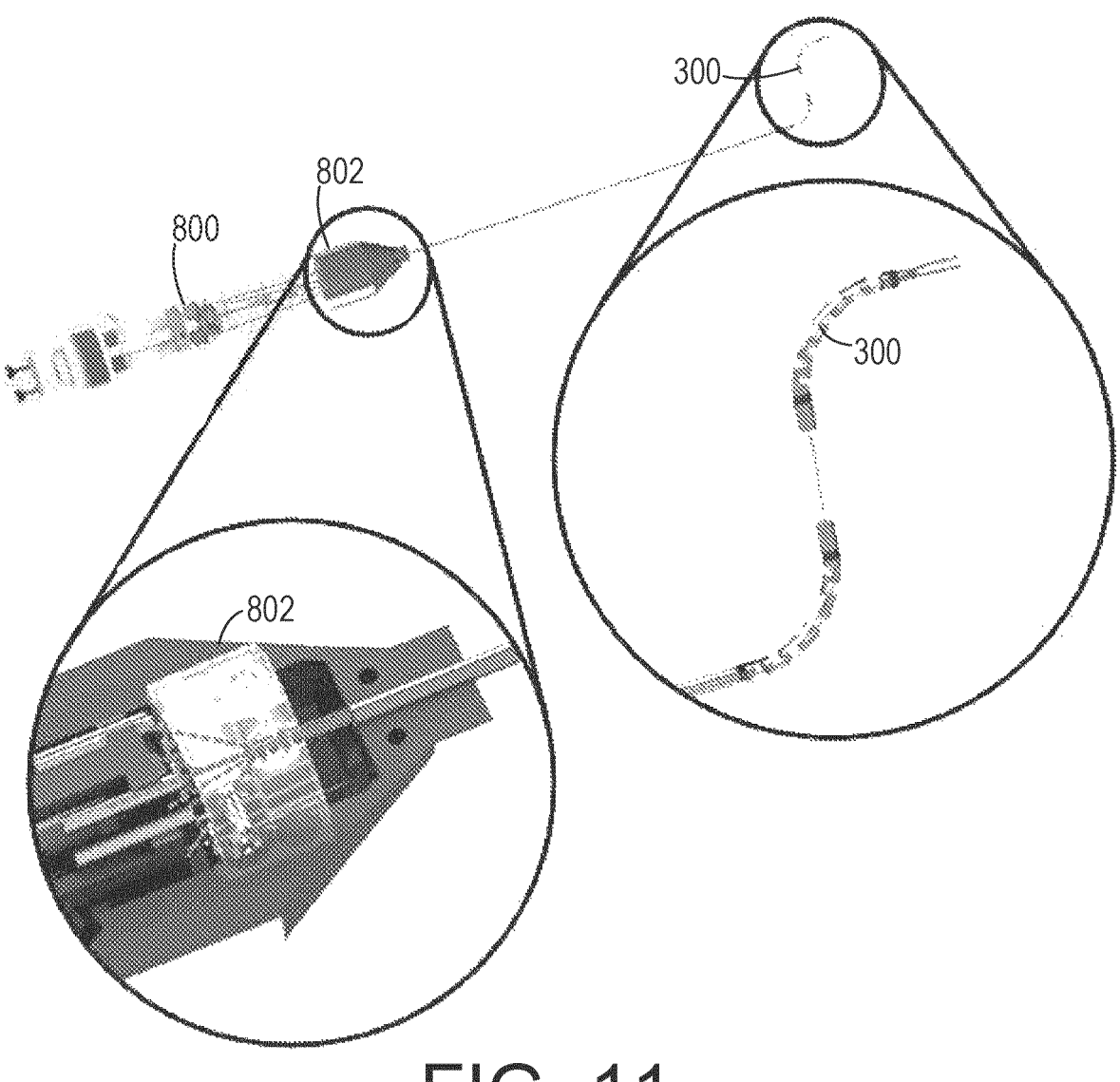
FIG. 11 is a detail of a probe coupled to a housing according to an exemplary embodiment of the present invention.
Figure 12:
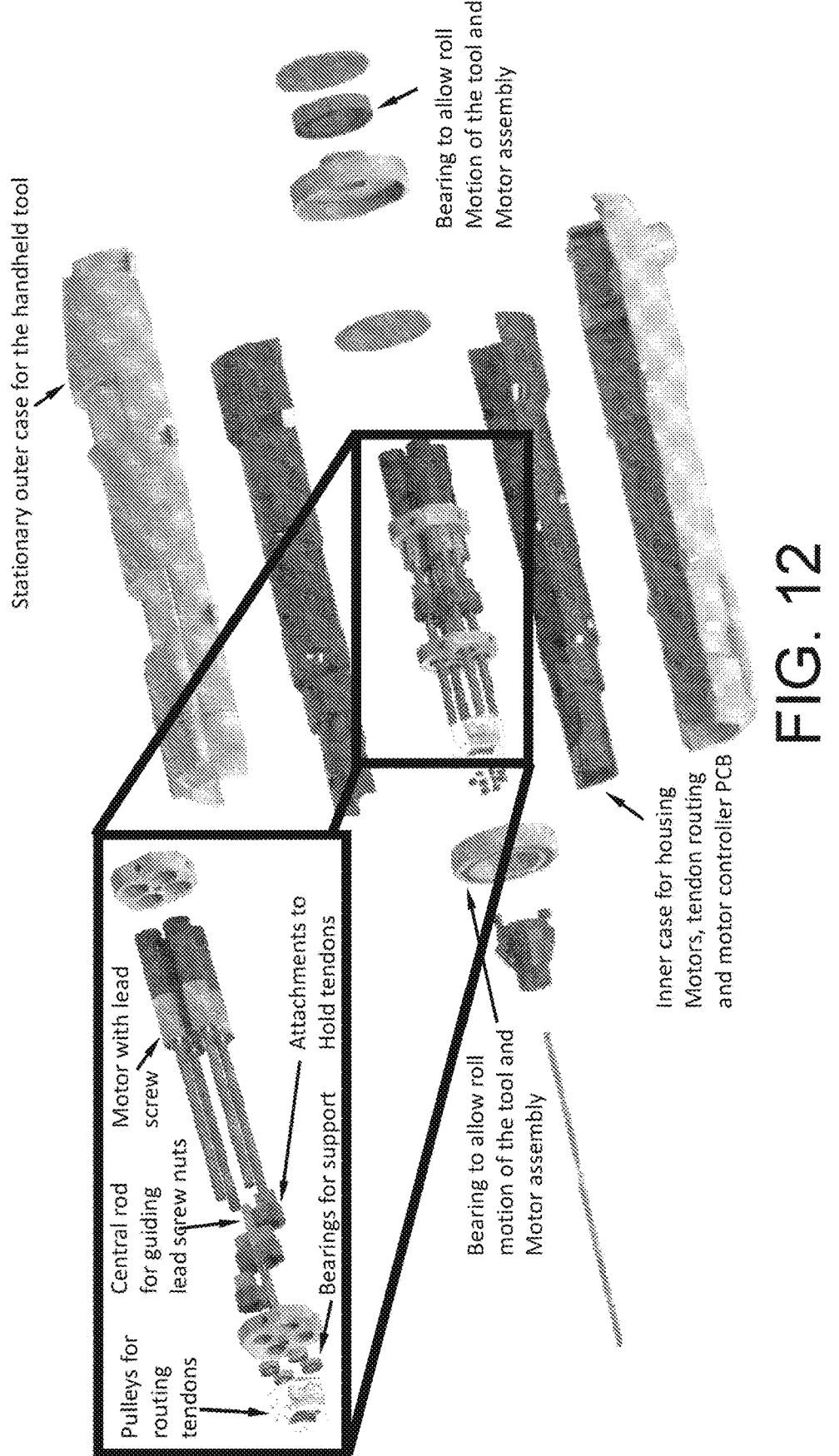
FIG. 12 is an exploded simulated drawing of a controller according to an exemplary embodiment of the present invention.
Figure 13:
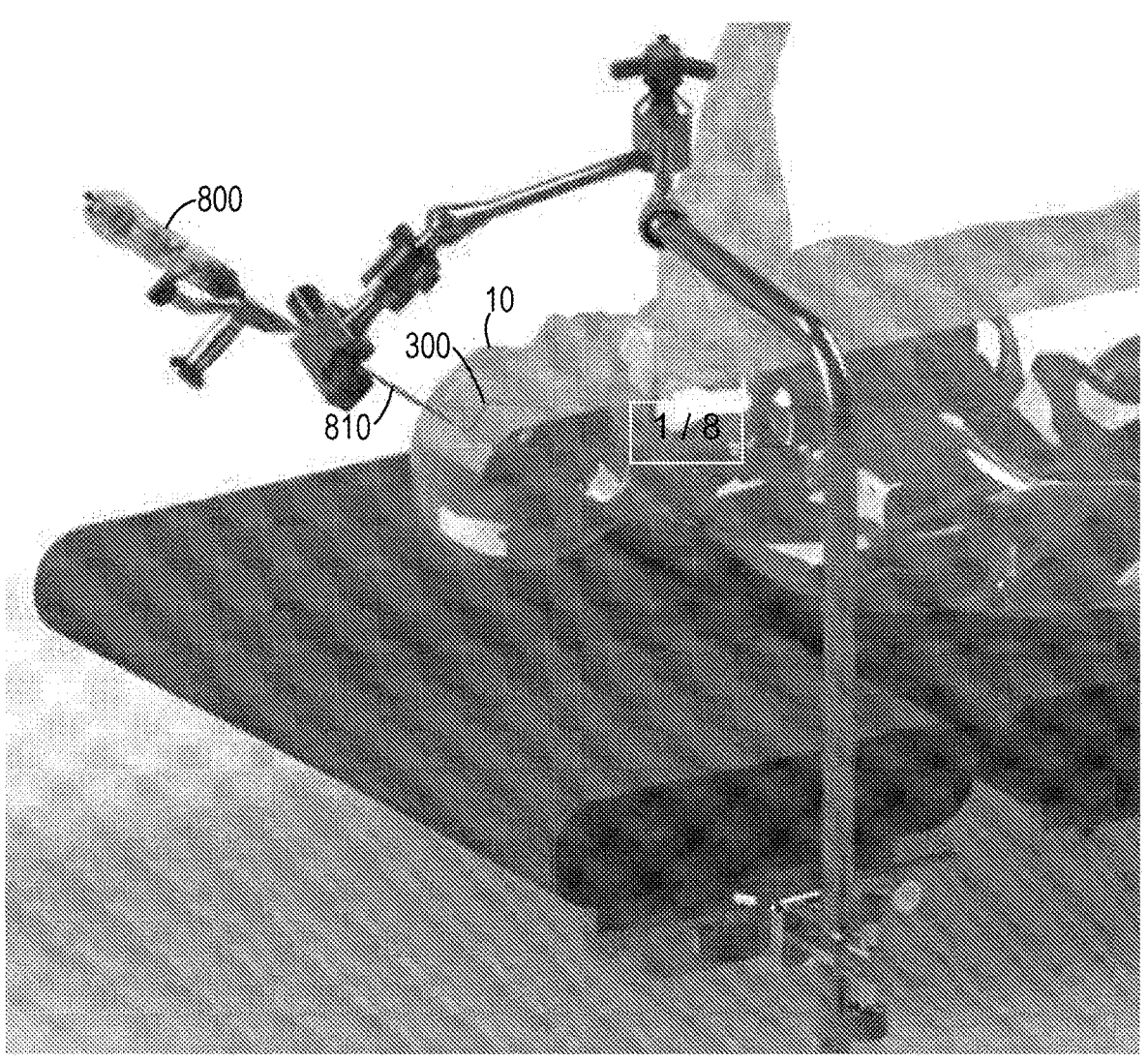
FIG. 13 is a simulated drawing demonstrating use of a probe and a housing being used with an endoscope according to an exemplary embodiment of the present invention.
Figure 14A:
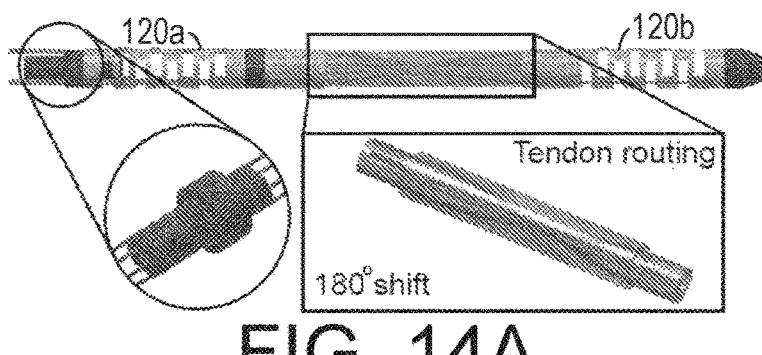
FIGS. 14A-14D are simulation drawings that show several different designs for a probe assembly according to an exemplary embodiment of the present invention.
Figure 14B:
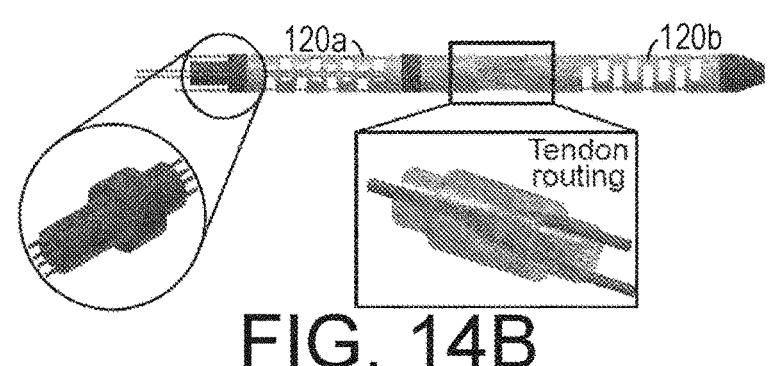
Figure 14C:
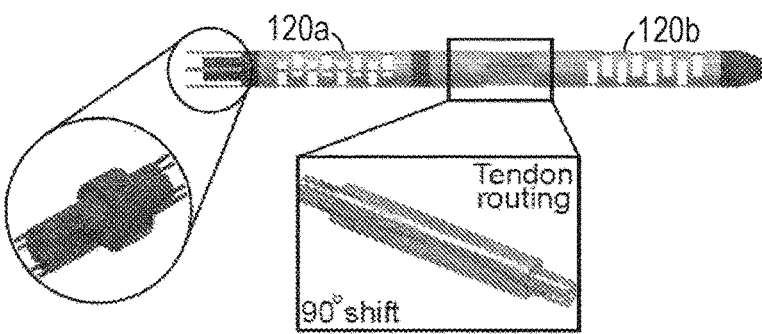
Figure 14D:
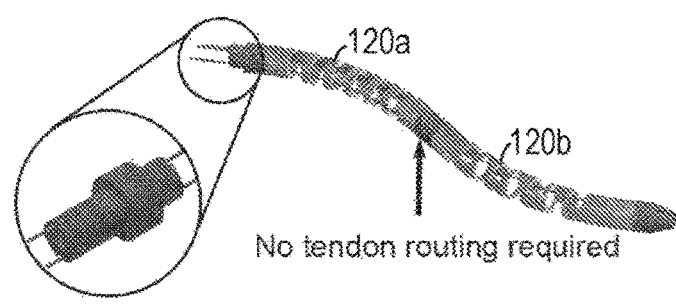

In another embodiment, the snapping and connection may occur magnetically. This quick connect assembly 802 allows for probes with different tools to be removed and preplaced within the endoscope during an operation. The controller 800 for operating the robotic tool tip should be in the range of existing devices used with commercially available endoscopes in terms of its size. Thus, in the experimental embodiment, the controller module has a diameter of 32 mm and length 178.85 mm, making it comparable to the size of existing products. This embodiment of the controller is easily able to dock itself into a connector module that interfaces with the MINOP neuroendoscope. This connector has a female socket that slides onto the neuroendoscope allowing for fine control of the tool tip position and the capability to be secured to the scope by a set screw for hands-free operation. The outer sheath of the controller also has a window for a clinician to be able to roll the entire motor and robot assembly along its central axis, to achieve yet another degree-of-freedom that is already available in existing devices. An exploded view of yet another embodiment of the controller is shown in FIG. 12. All of the joints for the designs are tendon driven. All tendons are controlled by prismatic actuation achieved by DC motors with lead screws. Individual joint tendons are routed via a pulley arrangement to a single DC motor, thereby employing two motors per joint. For designs using two-four tendons, the controller allows room for up to four DC Motors of diameter 8 mm (Maxon Precision Motors, MA, United States) with lead screws of length 50 mm and pitch 0.5 mm. All four lead screws are mounted with nuts that hold the tendons which are resting on a single central rod. This rod prevents the nuts from rotating, thereby causing them to slide along the length of this rod achieving prismatic motion. This entire motor and lead screw assembly is resting on two bearings at either end of the controller and is placed in an inner housing. These bearings therefore allow the housing to be rotated along the central axis of the entire cylindrical assembly allowing for the previously described rolling motion. A probe system of this type is shown in FIG. 11. This system in use during an operation is shown in FIG. 13.

Figure 15:
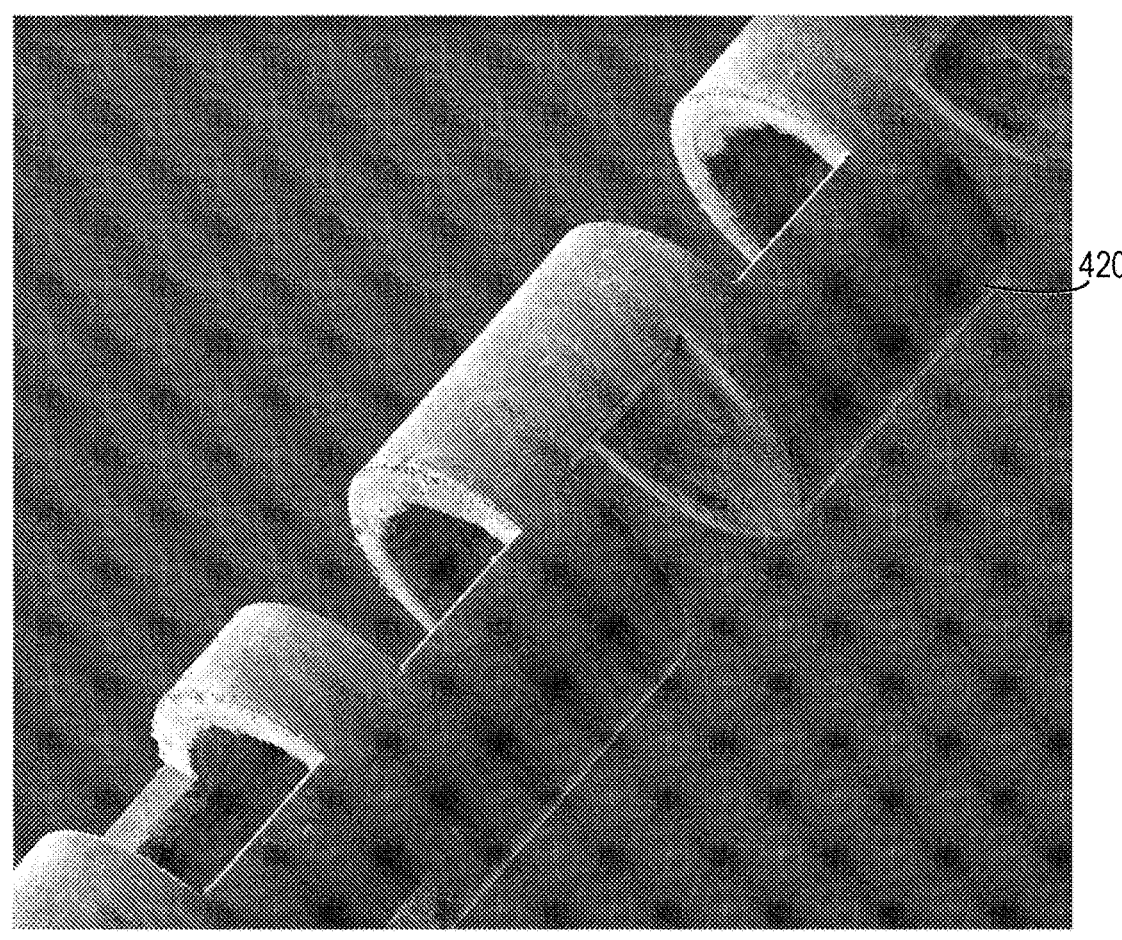
FIG. 15 is a micrograph of a crenulated nickel titanium alloy tube according to an exemplary embodiment of the present invention.

In one experimental embodiment, due to the size constraint on the robot diameter, bending flexural joints (elongated elastic members) were made by machining away material from a tube form a specific pattern. In one embodiment, unidirectional asymmetric notch joints were made by removing material from a tube in an asymmetric manner. However, it was found that when all notches lie on one side of the central axis of the tube resulted in the pushing of the neutral axis of the joint to the far end. This made the joint susceptible to transverse forces and other external forces. Bi-directional symmetric joints did not give rise to this issue, but they demonstrated a lack a high degree of compliance due to their limited moment arm. To keep compliance in the bending plane high, while keeping external forces low, a flexural joint known as the bidirectional asymmetric notch joint was adopted, as shown in FIG. 15. In this design, asymmetric notches were created on both sides of the central axis, to create a compliant bending segment between the notch. This type of a joint is capable of withstanding high axial forces as well as forces in the plane transverse to the bending plane. This ability of the notch joint to resist transverse forces allows a tendon routing strategy that minimizes inter-joint coupling.

Figure 16:
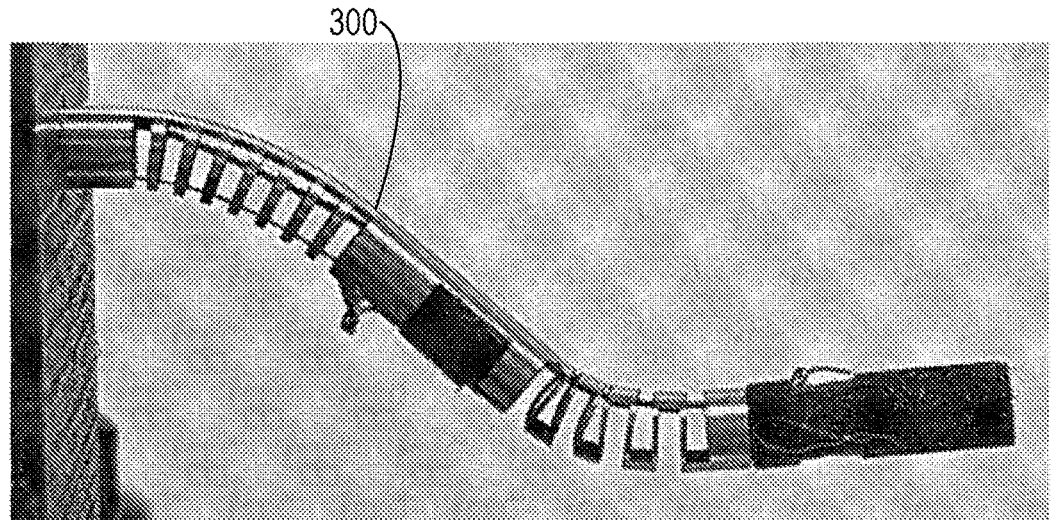
FIG. 16 is a photograph of an experimental embodiment of a probe assembly according to an exemplary embodiment of the present invention.

To manufacture the joints used in the experimental embodiment, nickel titanium alloy tubes of outer diameter (OD) of 2 mm and inner diameter (ID) of 1.43 mm (available from Confluent Medical, Calif., United States) were machined on a 3-axis CNC milling machine (available from Okuma Millac, Okuma America Corporation, N. C., United States) with a 500 micron diameter 4 flute end mill (available from Richards Micro Tool 875-TJ-0.020, Mass., United States). The nominal cutting speed was 19 m/min. and the feed rate was 4.2 mm/sec. In another embodiment of the robot, the joints of the robot were manufactured from nickel titanium alloy tubes of 1.93 mm in outer diameter (OD) and 1.49 mm in inner diameter. Micromachining of the crenulations was performed on a femtosecond laser (WS-Flex Ultra-Short Pulse Laser Workstation, available from Optec, Frameries, Belgium). The robotic probe assembly itself included two joints, both bending in the same plane along parallel axes, and both tendon-driven. Each joint could be deflected in each direction in its bending plane by two tendons. However, the two tendons that drive the distal joint were routed along with the tendons driving the proximal joint. The distal joint tendons were routed on a plane transverse to the bending plane of the proximal joint. Since the proximal joint was designed to have high compliance in its bending plane but low compliance in its transverse plane, actuating the distal tendons did not cause significant deflection of the proximal joint, thus achieving decoupling by design. The tendon phase shifter block was a 3D printed tube with 0.2 mm channels spiraling inside it to allow the distal tendons to shift in phase (by) 90° so that that they could move from the transverse plane to the bending plane of the distal joint. This resulted in a tendon-driven multi-degree of freedom (DoF) system that achieved decoupling by the usage of directionally compliant spring-like joints, and a tendon routing scheme between consecutive joints, as shown in FIG. 16.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and conducted in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for conducting the several purposes of the embodiments and claims presented in this application. It is important, therefore, that the claims be regarded as including such equivalent constructions.

Furthermore, the purpose of the foregoing Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way. Instead, it is intended that the present invention is defined by the claims appended hereto.

What is claimed is:

1. A probe assembly comprising:

a base member defining a first bore and a spaced apart second bore passing therethrough;

a first elongated elastic member:

having a first side and an opposite second side;

including a near end secured to the base member and extending therefrom to a far end; and defining a first channel in communication with the first bore running lengthwise along the first elongated elastic member;

one or more additional elongated elastic members coupled in series to the first elongated elastic member, each additional elongated elastic member:

having a first side and an opposite second side;

including a near end and extending to an opposite far end; and defining an additional channel running lengthwise along the additional elongated elastic member;

an intermediate rigid member affixed to the far end of the first elongated elastic member;

a first tendon having a first end located outside the base member, the first tendon having a portion which is disposed through the first bore which is adjacent to the first side of the first elongated elastic member, and the first tendon having a portion extending to an opposite second end located within the first channel of the first elongated elastic member, the second end of the first tendon being secured to the first elongated elastic member adjacent to the far end, the first tendon exiting through the first bore so that the first end extends outwardly therefrom, such that applying tension to the first tendon causes the first elongated elastic member to bend in a direction of the first side of the first elongated elastic member; and a second tendon having a first end located outside the base member, the second tendon having a portion which is disposed through the second bore which is adjacent to the second side of the first elongated elastic member, and the second tendon having a portion extending to an opposite second end located within the first channel of the first elongated elastic member, the second end of the second tendon being secured to the first elongated elastic member adjacent to the far end, the second tendon exiting through the second bore so that the first end extends outwardly therefrom, such that applying tension to the second tendon causes the first elongated elastic member to bend in a direction of the second side of the first elongated elastic member.

2. The probe assembly of claim 1 further comprising: a third tendon;

wherein:

a first of the one or more additional elongated elastic members is a second elongated elastic member; and the third tendon having a first end located outside the base member, the third tendon having a portion which is disposed through a third bore in the base member, which is adjacent to the first side of the second elongated elastic member, and the third tendon having a portion extending to an opposite second end located within the additional channel of the second elongated member, the second end of the third tendon secured to the second elongated elastic member adjacent to the far end, the third tendon exiting through the third bore so that the first end extends outwardly therefrom, such that applying tension to the third tendon causes the second elongated elastic member to bend in the direction of the first side of the second elongated elastic member.

3. The probe assembly of claim 2 further comprising:

a fourth tendon having a first end located outside the base member, the fourth tendon having a portion which is disposed through a fourth bore in the base member, which is adjacent to the second side of the second elongated elastic member, and the fourth tendon having a portion extending to an opposite second end located within the additional channel of the second elongated member, the second end of the fourth tendon secured to the second elongated elastic member adjacent to the far end, the fourth tendon exiting through the fourth bore so that the first end extends outwardly therefrom, such that applying tension to the fourth tendon causes the second elongated elastic member to bend in the direction of the second side of the second elongated elastic member.

4. The probe assembly of claim 3, wherein the probe assembly has a diameter that is less than a working channel of a rigid endoscope.

5. The probe assembly of claim 3, wherein:

the first elongated elastic member further comprises a first tube including a first tube first plurality of crenulations machined into the first side of the first elongated elastic member; and the second elongated elastic member further comprises a second tube including a second tube first plurality of crenulations machined into the first side of the second elongated elastic member.

6. The probe assembly of claim 5, wherein:

the first tube further includes a first tube second plurality of crenulations machined into the second side of the first elongated elastic member; and the second tube further includes a second tube second plurality of crenulations machined into the second side of the second elongated elastic member.

7. The probe assembly of claim 3 further comprising a tool affixed to the far end of the second elongated elastic member.

8. A probe system comprising:

the probe assembly of claim 1; and a device configured to operate the probe assembly;

wherein:

the device is further configured to be used with an endoscope that defines a lengthwise passage passing therethrough;

the device comprises:

a housing having an interior that is configured to be accessed by retracting a retractable portion, the housing further having an end that is configured for joining with the endoscope;

at least one input passage defined by the housing and configured to be aligned with the lengthwise passage of the endoscope, the at least one input passage configured to receive a portion of the probe assembly therein so that the probe assembly is received into the lengthwise passage of the endoscope; and an actuator assembly affixed to the housing and configured to manipulate the probe assembly by selectively applying stress to one or more of the first or second tendons.

9. The probe system of claim 8, wherein the device further comprises:

a quick connect assembly couplable to the actuator assembly and affixed to the probe assembly;

wherein:

one or more of the first or second tendons is coupled to a probe-side tendon connector; and the actuator assembly includes an actuator-side tendon connector that is complimentary to the probe-side tendon connector so that when the quick connect assembly is snapped in place with the actuator assembly, the actuator-side tendon connector engages the probe-side tendon connector so that actuator-induced movements applied to the actuator-side tendon connector results in corresponding movements in the probe-side tendon connector, thereby resulting in manipulation of the one or more of the first or second tendons.

10. The probe system of claim 9 further comprising:

at least one joystick configured to provide intuitive control input to the probe assembly.

* * * * *